United States Patent [19]

Wilkerson

[11] Patent Number: 5,021,455

[45] Date of Patent: Jun. 4, 1991

[54] SOLUTION FOR NEUTRALIZING CAUSTIC EFFECTS OF ALKALINE CEMENTITIOUS MATERIALS ON HUMAN SKIN

[76] Inventor: Gary C. Wilkerson, P.O. Box 414, Paradise, Calif. 95967

[21] Appl. No.: 451,139

[22] Filed: Dec. 15, 1989

[51] Int. Cl.$^5$ .................. A61K 31/19; A61K 31/185; A61K 49/00

[52] U.S. Cl. .................................. 514/574; 514/578; 514/553; 424/10

[58] Field of Search ....................... 514/574, 578, 553; 424/10

[56] References Cited

U.S. PATENT DOCUMENTS

| | | | |
|---|---|---|---|
| 3,993,750 | 11/1976 | Fox, Jr. ................................. | 524/601 |
| 4,105,782 | 8/1978 | Yu et al. .............................. | 514/613 |
| 4,197,316 | 4/1980 | Yu et al. .............................. | 514/554 |
| 4,363,815 | 12/1982 | Yu et al. .............................. | 514/263 |
| 4,855,130 | 8/1989 | Konrad et al. ....................... | 424/70 |

Primary Examiner—Richard L. Raymond
Assistant Examiner—Gary E. Hollinden

[57] ABSTRACT

An aqueous solution containing a mild concentration of organic acids, vitamin E acetate and a low concentration of aromatic oil to neutralize the caustic effects of alkaline cementitious materials such as concrete, stucco and the like on human skin. The solution restores a normal pH balance to the skin of those who have been exposed to either dry or wet alkaline cementitious materials.

26 Claims, No Drawings

SOLUTION FOR NEUTRALIZING CAUSTIC EFFECTS OF ALKALINE CEMENTITIOUS MATERIALS ON HUMAN SKIN

BACKGROUND OF THE INVENTION

1. Field of the invention

This invention consists of a skin treatment solution designed to neutralize and compensate the negative physiological action of alkaline cementitious materials on the human skin.

2. Description of the Prior Art

Hydraulic cement, particularly Portland cement which has an alkaline pH of 11 to 13 is used in a variety of products such as concrete, stucco, plaster and grout for construction of such structures as sidewalks, brick walls, slab floors, and tile counter-tops to name just a few. Primarily due to its alkalinity, hydraulic cement and cementitious materials made with hydraulic cement are considered to a hazardous substance when in sustained contact with human skin.

The authoritative data on the acid/base characteristics of the human skin (epidermis) indicate that the surface of the skin is slightly acidic, having a pH of 4.0 to 6.0. This pH range is optimal to maintain epidermal cell integrity and maximize the functionality of the resident epidermal flora of micro-organisms that protect the body surface from invasion of foreign species that can cause infection. Normal epidermis has considerable ability to maintain the normal acid/base balance (buffer capacity). However, if exposure to excessive and persistent alkalinity is beyond the normal buffer capacity, the skin does not have the resources to maintain its normal integrity. This insult leads to perceptible epidermal water loss and destruction of the normal components of intercellular adhesives that create a epidermal environment leading to dry, chapped, fissured and flaking skin.

The degree of manual dexterity required by workmen working with such materials generally prohibits the use of gloves and protective arm wear. Therefore, while working with these alkaline cementitious materials, whether a dry powder or a wet mixture, the materials adhere on the hands and arms of the workers. The alkaline cementitious materials work into the pores of the skin, and residual amounts can remain even after washing with water. Cementitious materials cure by hydration, a chemical process requiring water which may be taken from any available source such as the skin. The curing process of residual amounts of cementitious material on the skin can leach moisture and the natural oils of the skin. The alkalinity of the hydraulic cement dehydrates and disrupts the normally acidic pH of the skin, leaving it generally chapped and irritated in the least. The effects of accumulation of this un-neutralized caustic material in the skin may lead to a variety of conditions ranging from mild skin irritation, to the development of open skin sores, to toxic reactions. The duration of exposure to these caustic materials determines the amount of harm to be done to the skin. Once the caustic materials work into the skin, the curing process will continue deteriorating the skin until the caustic materials are neutralized.

While the application of general purpose hand lotions and creams, or even water provide limited relief to the irritated skin, they are not formulated with the objective of quickly and adequately neutralizing the caustic effects of cementitious materials. Available hand creams and lotions unfortunately leave an oily film on the hands which make gripping of various tools difficult. The oily film from hand creams also has a tendency to cause a more rapid accumulation of dry cementitious materials on the skin, and therefore cannot be used during work.

I know of no past art skin treatment solution which similarly addresses the above problems associated with exposure of the skin to caustic alkaline cementitious materials of the types used in the building trades.

SUMMARY OF THE INVENTION

In practicing my invention, I have developed a product formula in the form of a skin treatment solution which contains organic acids specifically for neutralizing the alkali found in cementitious materials of the types used in the building trades such as concrete and stucco. With the use of this skin treatment, the curing process of the cement is generally arrested and the skin is restored to its normal pH balance. The formula is a non-greasy fluid which quickly penetrates the pores of the skin to readily supply an acidic solution to neutralize the alkaline cementitious materials on and in the skin. The alkaline cementitious material is neutralized using the more readily available acid and moisture of the invention rather than the natural acids and moisture of the skin. My formula also contains enough Lemon oil and Vitamin E Acetate to help restore and maintain the pliability of the skin, yet maintaining the non-greasy characteristic, allowing for proper gripping of hand tools. The skin treatment solution is simply sprayed or poured onto the skin which has been exposed to the cementitious materials. The liquid is then rubbed into the skin and left without rinsing. The preferred method of use is to apply the treatment within about two hours of exposure to the alkaline cementitious material, reapply the treatment about every 2 hours during work, and then finally apply once after work. The acidity of the solution is sufficiently buffered as to generally not cause any skin irritation even in the absence of any alkaline substances on the skin.

It is therefore a primary object of the invention to provide a skin treatment solution to neutralize the caustic effects of alkaline cementitious materials of the types typically used in the building trades which contact the skin in order to maintain the skin in a healthy condition even with repeated exposure to the caustic materials.

A further object of the invention to achieve the above in a non-greasy formula which allows non-slip gripping of hand tools immediately after use of the treatment.

A further object of the invention is to achieve the above in a treatment which is convenient and simple to use.

Other objects are to achieve the above with a skin treatment which is safe, ecologically compatible, efficient, inexpensive, and does not require skilled application or a doctor's prescription to use.

The specific nature of the invention, as well as other objects and advantages thereof, will clearly appear from the following description and examples.

BEST MODE FOR CARRYING OUT THE INVENTION

The skin treatment consists of applying an aqueous solution containing organic acids to neutralizes the alkali found in cementitious materials. The acid of the slightly acidic solution is buffered desirably with Sodium citrate so as to generally not irritate the skin even in the absence of any alkaline cementitious material thereon. An organic preservative such as sorbates or parabens is included to give the product a safe and effective shelf life. A small quantity of Vitamin E Acetate is included in the solution since it is known to be healthful to the skin. In order to replenish lost oils to the skin to aid in maintaining its pliability, a small amount of Lemon oil or other aromatic oil is added to the solution. The aromatic oil also adds a pleasant smell to the formula. A solubilizer such as Polysorbate 20 is added to assure compatibility of the aromatic oil and Vitamin E Acetate with the remainder to the solution. To bring the solution to a proper acidic pH level, both Citric acid and Acetic acid are used. It will be recognised by those skilled in the art that a wide variety of acids such as lactic acid or tartaric acid could be used, however I have found Citric acid to be safe, natural, and inexpensive. The Acetic acid is used mainly to change the scent of the solution from that of using pure Citric acid and aromatic oil.

The following examples are meant to illustrate preferred formulations of the invention but are in no way intended to limit its scope. The percentages given are by weight.

EXAMPLE #1

Of a given weight of the product, the following would generally constitute the preferred formula starting with water being about 94.54 percent of the solution having in it Sodium citrate, being 1 percent, Polysorbate 20, being 1 percent, Potassium sorbate, being 0.25 percent, Lemon oil, being 0.1 percent, Vitamin E Acetate, being 0.01 percent, Citric acid, being 3 percent, and Acetic acid, being 0.1 percent.

EXAMPLE #2

Of a given weight of the product, the following would generally constitute a suitable alternative formula starting with water being about 94.65 percent of the solution having in it Lactic acid, being 2.5 percent, Potassium lactate, being 1.5 percent, Poloxamer 188, being 1 percent, Methyl paraben, being 0.2 percent, Peppermint oil, being 0.05 percent, and Vitamin E Acetate being 0.1 percent.

Some variations in the specific ingredients and their percentages of the total have been tried with a degree of success. However, a solution resultant from one of the above formulations has been found to function well and to be pleasant to use for the intended purpose. These formulas are generally regarded as non-toxic if ingested, and non-flammable. If one does get the product in an eye, thorough flushing with water is usually all that is necessary to relieve possible minor irritation.

The preferred method for applying the solution is from a spray bottle, making it easy to apply the solution evenly before rubbing into the skin.

It is realized those skilled in the art will, after reading this disclosure will be able to make modifications to the formulas herein disclosed. The formulas herein disclosed are for example only, and are in no way intended to limit the scope of the appended claims. Therefore, modification to the formula made by others which fall into the scope of my appended claims will be considered my invention.

What I claim as my invention is:

1. A method of treating the caustic effects of alkaline cementitious materials on human skin which comprises administering an effect amount of a composition which comprises a non-caustic acid to said human skin.
2. A method according to claim 1 wherein said non-caustic acid is citric acid.
3. A method according to claim 1 wherein said non-caustic acid is acetic acid.
4. A method according to claim 1 wherein said composition further includes vitamin E acetate.
5. A method according to claim 1 wherein said composition further includes aromatic oil.
6. A method according to claim 1 wherein said composition further includes a buffer.
7. A method according to claim 1 wherein the acids comprise 2 to 10 percent by volume.
8. A method according to claim 1 wherein the acids comprise 2 to 20 percent by volume.
9. A method according to claim 1 wherein the pH is 3 to 8.
10. A method according to claim 1 wherein the pH is 4 to 7.
11. A method according to claim 1 wherein said composition is administered during the period of exposure to caustic materials.
12. A method according to claim 1 wherein said composition is administered after exposure to caustic materials.
13. A method of preventing degeneration due to repeated exposure to the caustic effects of alkaline cementicious materials on human skin which comprises administering an effective amount of a composition which comprises a non-caustic acid to said human skin.
14. A method according to claim 13 wherein said non-caustic acid is citric acid.
15. A method according to claim 13 wherein said non-caustic acid is acetic acid.
16. A method according to claim 13 wherein said composition further includes vitamin E acetate.
17. A method according to claim 13 wherein said composition further includes aromatic oil.
18. A method according to claim 13 wherein said composition further includes a buffer.
19. A method according to claim 13 wherein the acids comprise 2 to 10 percent by volume.
20. A method according to claim 13 wherein the acids comprise 2 to 20 percent by volume.
21. A method according to claim 13 wherein the pH is from 3 to 8.
22. A method according to claim 13 wherein the pH is from 4 to 7.
23. A method according to claim 13 wherein said composition is administered before exposure to caustic materials.
24. A method according to claim 13 wherein said composition is administered during exposure to caustic materials.
25. A method according to claim 13 wherein said composition is administered after exposure to caustic materials.
26. A method according to claim 1 wherein aid composition is administered before exposure to caustic materials.

* * * * *